US012788460B2

(12) United States Patent
Tromer et al.

(10) Patent No.: US 12,788,460 B2
(45) Date of Patent: Nov. 10, 2026

(54) CONNECTIVE TISSUE REPAIR SUTURE ANCHOR DEVICE

(71) Applicant: Tendonplus Medical Pte. Ltd., Singapore (SG)

(72) Inventors: Dotan Tromer, Moshav Hosen (IL); Nir Goldenberg, Zoran (IL); Chung Hui Tan, Singapore (SG); Zai Hong Kua, Singapore (SG)

(73) Assignee: Tendonplus Medical Pte. Ltd., Singapore (SG)

( * ) Notice: Subject to any disclaimer, the term of this patent is extended or adjusted under 35 U.S.C. 154(b) by 307 days.

(21) Appl. No.: 18/353,180

(22) PCT Filed: Jan. 11, 2022

(86) PCT No.: PCT/IB2022/050186

§ 371 (c)(1),
(2) Date: Jul. 17, 2023

(87) PCT Pub. No.: WO2022/153176

PCT Pub. Date: Jul. 21, 2022

(65) Prior Publication Data

US 2024/0122633 A1 Apr. 18, 2024

Related U.S. Application Data

(60) Provisional application No. 63/138,580, filed on Jan. 18, 2021.

(51) Int. Cl.
*A61B 17/84* (2006.01)
*A61B 17/04* (2006.01)

(52) U.S. Cl.
CPC .... *A61B 17/844* (2013.01); *A61B 2017/0409* (2013.01); *A61B 2017/0464* (2013.01)

(58) Field of Classification Search
CPC .... A61B 2017/0404; A61B 2017/0414; A61B 2017/0403; A61B 2017/0406
See application file for complete search history.

(56) References Cited

U.S. PATENT DOCUMENTS 6,117,161 A * 9/2000 Li ...................... A61B 17/0401 606/232
6,132,442 A * 10/2000 Ferragamo ............ A61F 2/0811 606/328

(Continued)

FOREIGN PATENT DOCUMENTS

GB 2288737 11/1995
WO 2019/164853 8/2019

OTHER PUBLICATIONS

PCT Search Report and Written Opinion PCT/IB2022/050186, Apr. 11, 2022.

*Primary Examiner* — Alexander J Orkin
(74) *Attorney, Agent, or Firm* — AlphaPatent Associates Ltd.; Daniel J. Swirsky

(57) ABSTRACT

A connective tissue repair device (10) includes a central hub member (12) formed with an aperture, and first and second anchoring members (14, 16) that extend from opposing sides of the central hub member (12). The first and second anchoring members (14, 16) each have a depth that extends between edges, one of the edges being sharp for pushing into tissue.

8 Claims, 3 Drawing Sheets

(56) References Cited

U.S. PATENT DOCUMENTS

| | | | | |
|---|---|---|---|---|
| 6,231,581 | B1 * | 5/2001 | Shank | A61B 17/064 606/157 |
| 6,569,186 | B1 * | 5/2003 | Winters | A61B 17/1735 606/232 |
| 6,746,450 | B1 * | 6/2004 | Wall | A61B 17/7059 606/280 |
| 10,231,767 | B2 * | 3/2019 | Campbell | A61B 17/809 |
| 2002/0022861 | A1 * | 2/2002 | Jacobs | A61B 17/064 606/213 |
| 2003/0105464 | A1 * | 6/2003 | Schreurs | A61B 17/809 606/300 |
| 2008/0082124 | A1 * | 4/2008 | Hess | A61B 17/07207 606/219 |
| 2009/0020584 | A1 * | 1/2009 | Soltz | A61B 17/0644 227/175.1 |
| 2012/0078371 | A1 * | 3/2012 | Gamache | A61B 17/0682 623/17.16 |
| 2012/0130374 | A1 * | 5/2012 | Bouduban | A61F 2/0805 606/75 |
| 2013/0267956 | A1 * | 10/2013 | Terrill | A61B 17/68 606/75 |
| 2017/0333039 | A1 * | 11/2017 | Leung | A61F 13/01038 |
| 2019/0350695 | A1 | 11/2019 | Blacklidge | |

* cited by examiner

CONNECTIVE TISSUE REPAIR SUTURE ANCHOR DEVICE

FIELD OF THE INVENTION

The present invention relates generally to surgical repair devices, and particularly to a device for tendon and/or ligament or any other kind of connective tissue repair, such as but not limited to, rotator cuff repair.

BACKGROUND OF THE INVENTION

Connective tissue damage or degeneration in the rotator cuff of a shoulder often requires surgical repair, including partial or complete reattachment of torn or detached connective tissue to bone. The terms connective tissue and soft tissue are used interchangeably herein and encompass, among other things, tendons and ligaments. The terms suture anchor and suture anchor device are used interchangeably herein. Conventional suture anchors are devices that are typically implanted in bore holes drilled into bone, and which have conventional surgical sutures affixed in some manner thereto. The suture anchors typically have features which cause the anchors to be engaged in the bone bore hole.

Arthroscopic rotator cuff repair procedures can be performed using open or arthroscopic surgical techniques and procedures, but are typically with minimally invasive arthroscopic methods.

There are some known problems associated with arthroscopic rotator cuff repair procedures. For example, a suture used to attach torn rotator cuff soft tissue to a suture anchor may cut through the reattached tissue under stress ("cheese wire effect"). In addition, it may be very difficult or cumbersome to tie the tendon properly to a surgical implant.

Thus, a significant need exists for improved apparatus for arthroscopic rotator cuff repair that overcomes problems of the prior art.

SUMMARY

The present invention seeks to provide a suture anchor device for connective tissue repair, e.g., tendon and/or ligament repair, such as but not limited to, rotator cuff repair, as is described more in detail hereinbelow. The invention is particularly applicable for rotator cuff repair, but can be used in the repair of many other ligaments and tendons or other connective tissue, such as in other joints in the body.

There is provided in accordance with a non-limiting embodiment of the present invention a connective tissue repair device including a central hub member formed with an aperture, and first and second anchoring members that extend from opposing sides of the central hub member, wherein the first and second anchoring members each have a depth that extends between edges, one of the edges being sharp for pushing into tissue.

In accordance with a non-limiting embodiment of the present invention the first and second anchoring members are mirror images of each other about a longitudinal and/or latitudinal axis of the connective tissue repair device.

In accordance with a non-limiting embodiment of the present invention the first and second anchoring members are arcuate, such as partial circles or ellipses.

In accordance with a non-limiting embodiment of the present invention the hub member includes sharp edges adjacent the sharp edges of the first and second anchoring members.

In accordance with a non-limiting embodiment of the present invention the sharp edges of the hub member and the sharp edges of the first and second anchoring members form one continuous sharp edge.

In accordance with a non-limiting embodiment of the present invention the first and second anchoring members are formed with one or more apertures.

In accordance with a non-limiting embodiment of the present invention the connective tissue repair device is coupled to a cover plate.

In accordance with a non-limiting embodiment of the present invention the connective tissue repair device may be used to repair connective tissue, such as a rotator cuff. Each of the first and second anchoring members of the connective tissue repair device may be pushed into tissue, for example, the greater tuberosity of the humeral head. Sutures may be used to tie the connective tissue repair device to connective tissue (such as the supraspinatus tendon of the rotator cuff) by passing the sutures through the central apertures of the hub members and tying to the connective tissue.

BRIEF DESCRIPTION OF THE DRAWINGS

The present invention will be understood and appreciated more fully from the following detailed description taken in conjunction with the drawings in which.

DETAILED DESCRIPTION

Figure 1:
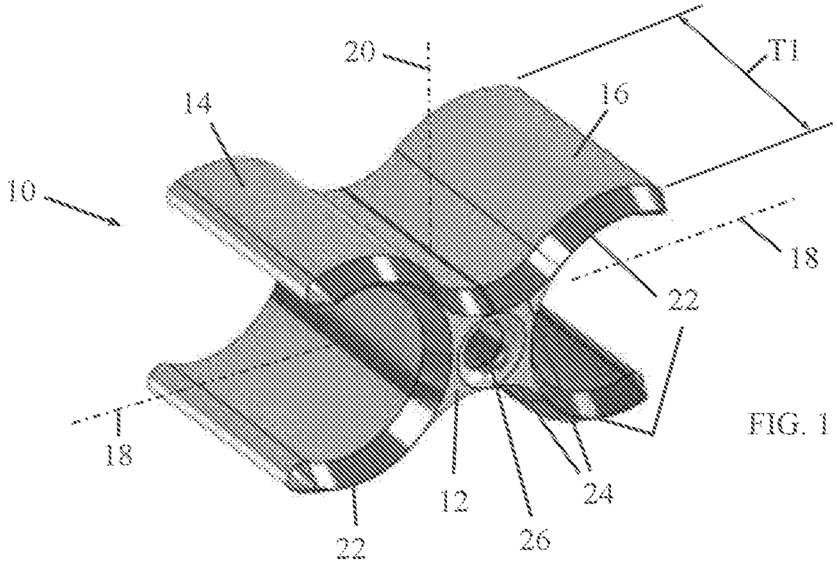
FIG. 1 is a simplified pictorial illustration of a connective tissue repair device, in accordance with a non-limiting embodiment of the present invention.

Reference is now made to FIG. 1, which illustrates a connective tissue repair device 10, in accordance with a non-limiting embodiment of the present invention.

The connective tissue repair device 10 may include a central hub member 12 and first and second anchoring members 14 and 16 that extend from opposing sides of central hub member 12. The connective tissue repair device 10 may have reflective symmetry about its central axis, that is, the first and second anchoring members 14 and 16 may be mirror images of each other, as seen in the illustrated embodiment. In the illustrated embodiment, the first and second anchoring members 14 and 16 are mirror images of each other about a longitudinal axis 18 and about a latitudinal axis 20 of the device 10.

Alternatively, the first and second anchoring members 14 and 16 may be shaped differently from each other and/or may have different sizes.

In the illustrated embodiment, the first and second anchoring members 14 and 16 are arcuate, such as being partial circles or ellipses or other arcuate shapes. The first and second anchoring members 14 and 16 have a depth or thickness (indicated by T1 in FIG. 1) that extends between edges 22, one of the edges preferably being sharp for pushing into tissue (the other side can have blunt edges to avoid damage to the user or other tissue). Hub member 12 may also include sharp edges 24 adjacent edges 22, and which may be continuous with edges 22 so to form one continuous sharp edge. The sharp edges allow the device 10 to be pushed into body tissue to anchor the device in the body.

Hub member 12 may be formed with a central aperture 26. Optionally, as seen in FIG. 2, each of the first and second anchoring members 14 and 16 may be formed with one or more apertures 28, through which blood vessels or tissues can pass.

The connective tissue repair device 10 may be constructed of any medically-safe, sturdy material, such as but not limited to, stainless steel, titanium alloy, plastics and others.

Figure 2:
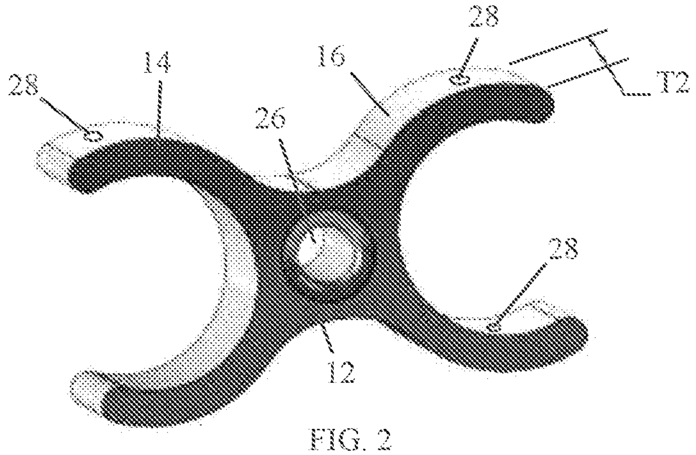
FIG. 2 is a simplified pictorial illustration of a connective tissue repair device, in accordance with another non-limiting embodiment of the present invention.

Reference is now made to FIG. 2, which illustrates another version of the connective tissue repair device, which is not as deep as in FIG. 1, but instead has a depth or thickness of T2, wherein T2<T1. Like elements are designated by like numerals. The connective tissue repair devices may be provided as a kit in an assortment of depths to cover many possible applications of the device.

Figure 3:
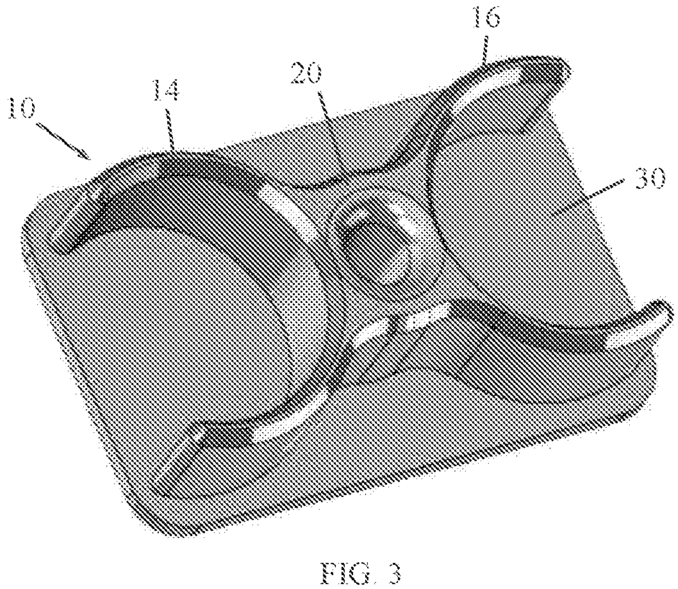
FIG. 3 is a simplified pictorial illustration of a connective tissue repair device, in accordance with another non-limiting embodiment of the present invention.

Reference is now made to FIG. 3, which illustrates another version of the connective tissue repair device 10, in accordance with a non-limiting embodiment of the present invention. In this version, connective tissue repair device 10 is coupled to a cover plate 30. Like elements are designated by like numerals. When the sharp edges of connective tissue repair device 10 are pushed into tissue, the cover plate 30 may serve as a stop to prevent device 10 from sinking further into the tissue.

Figure 5A:
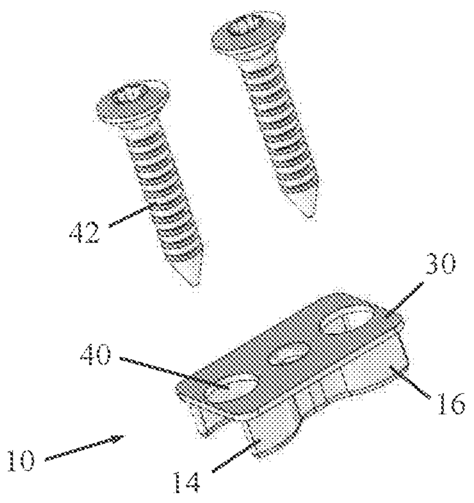
FIGS. 5A and 5B are simplified pictorial illustration of the connective tissue repair device, with the addition of fasteners in a cover plate, in accordance with another non-limiting embodiment of the present invention.
Figure 5B:
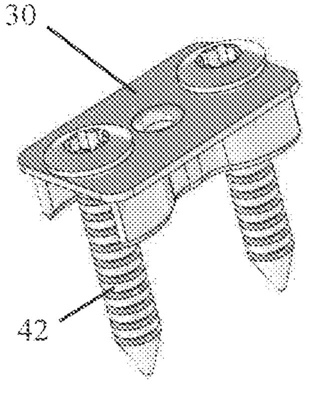

As seen in FIGS. 5A and 5B, cover plate may be formed with one or more mounting holes 40 for receiving therethrough one or more fasteners 42. Such an embodiment may be useful if the tendon itself has not been torn or broken, but rather has become detached just at the extremity above the humeral head. In such a case, the connective tissue repair device 10 may be pressed into the tendon, and fasteners 42 may clamp the device directly into the humeral head. In this manner, anchors and sutures are eliminated while tendon-to-bone interface stabilization is increased.

Figure 4:
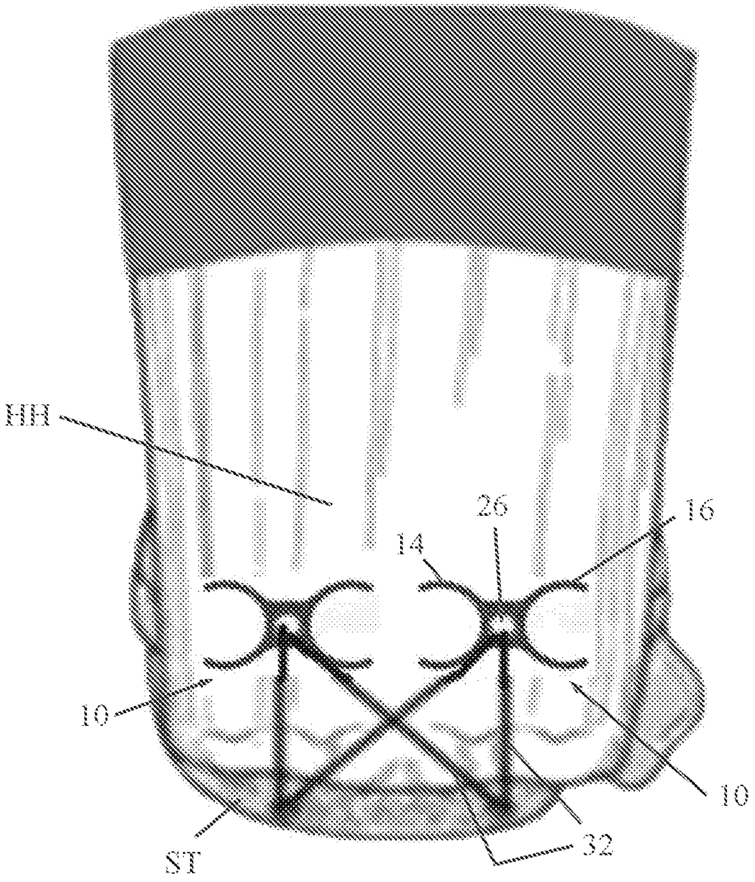
FIG. 4 is a simplified pictorial illustration of the connective tissue repair device used to repair connective tissue, such as a rotator cuff, in accordance with a non-limiting embodiment of the present invention.

Reference is now made to FIG. 4, which illustrates the connective tissue repair device 10 being used to repair connective tissue, such as a rotator cuff, in accordance with a non-limiting embodiment of the present invention.

Each of the first and second anchoring members 14 and 16 of connective tissue repair device 10 is pushed into tissue, in this example, the greater tuberosity of the humeral head (HH). Sutures 32 may be used to tie the connective tissue repair device 10 to connective tissue (such as the supraspinatus tendon (ST) of a rotator cuff) by passing the sutures through the central apertures 26 of hub members 12 and tying to the connective tissue.

What is claimed is:

1. A connective tissue repair device comprising:

a central hub member formed with an aperture; and first and second anchoring members that extend from opposing sides of said central hub member, wherein said first and second anchoring members each have a depth that extends between a sharp edge, which is sharp for pushing into tissue, and a dull edge, and said dull edges of said first and second anchoring members are coupled to a cover plate which has a perimeter that extends beyond perimeters of both of said first and second anchoring members, wherein the aperture of the central hub member is configured to receive a suture therethrough for tying the connective tissue repair device to connective tissue and wherein said hub member comprises sharp edges adjacent said sharp edges of said first and second anchoring members, said sharp edges of said hub member and said sharp edges of said first and second anchoring members form one continuous sharp edge.

2. The connective tissue repair device according to claim 1, wherein said first and second anchoring members are mirror images of each other about a longitudinal axis of said connective tissue repair device.

3. The connective tissue repair device according to claim 1, wherein said first and second anchoring members are mirror images of each other about a latitudinal axis of said connective tissue repair device.

4. The connective tissue repair device according to claim 1, wherein said first and second anchoring members are arcuate.

5. The connective tissue repair device according to claim 1, wherein said first and second anchoring members are partial circles or ellipses.

6. The connective tissue repair device according to claim 1, wherein said first and second anchoring members are formed with one or more apertures.

7. The connective tissue repair device according to claim 1, wherein said cover plate is a stop to prevent said first and second anchoring members from sinking into tissue beyond said depths.

8. The connective tissue repair device according to claim 7, wherein said cover plate is formed with one or more mounting holes.

* * * * *